United States Patent [19]
Hansen et al.

[11] Patent Number: 6,090,267
[45] Date of Patent: Jul. 18, 2000

[54] METHODS AND APPARATUS FOR QUANTITATIVE ANALYSIS OF A SAMPLE

[75] Inventors: Brian N. Hansen; Arnold E. Williams, both of Boulder, Colo.

[73] Assignee: Timberline Instruments, Inc., Boulder, Colo.

[21] Appl. No.: 09/118,023

[22] Filed: Jul. 17, 1998

Related U.S. Application Data

[60] Provisional application No. 60/053,022, Jul. 18, 1997.
[51] Int. Cl.[7] .......................... G01N 27/404; G01N 27/06
[52] U.S. Cl. ...................... 205/780.5; 204/409; 204/415; 204/431; 205/781; 205/783; 324/71.1; 324/439; 422/68.1; 422/82.01; 422/82.02; 422/98
[58] Field of Search .................................. 204/415, 431, 204/432, 409; 205/780.5, 781, 782, 782.4, 783; 422/81, 82, 82.01, 82.02, 98, 68.1; 324/71.1, 439

[56] References Cited

U.S. PATENT DOCUMENTS

| | | | |
|---|---|---|---|
| 3,869,354 | 3/1975 | Montalvo | 204/415 |
| 3,950,231 | 4/1976 | Frant et al. | 205/780.5 |
| 4,209,299 | 6/1980 | Carlson | 422/98 |
| 4,849,058 | 7/1989 | Driscoll et al. | 205/781 |
| 5,525,197 | 6/1996 | Coulson | 205/780.5 |

*Primary Examiner*—T. Tung
*Attorney, Agent, or Firm*—Dinsmore & Shohl LLP

[57] ABSTRACT

Methods for determining the amount of volatile electrolyte present in an aqueous liquid sample comprise transferring the electrolyte from the aqueous liquid sample to an absorber solution across a gas-permeable membrane which is non-passable to the aqueous liquid sample and measuring the change in electrical conductivity of the absorber solution during the transfer period. The absorber solution contains a solute which enhances the transfer of the electrolyte. Apparatus for conducting such methods include an absorber solution containing a solute which enhances the transfer of the electrolyte.

28 Claims, 4 Drawing Sheets

6,090,267

METHODS AND APPARATUS FOR QUANTITATIVE ANALYSIS OF A SAMPLE

This application is accorded the benefit of provisional application Ser. No. 60/053,022, filed Jul. 18, 1997.

FIELD OF THE INVENTION

The present invention is directed to methods and apparatus for quantitatively analyzing a sample, and particularly to such methods and apparatus which employ electrical conductivity measuring techniques to determine the amount of a volatile or nonvolatile substance in a sample.

BACKGROUND OF INVENTION

Quantitative analysis of liquid samples using electrical conductivity measurements is known in the art. Previously, two-cell conductivity detectors were often used. In such apparatus, the conductivity measurement is based on the difference in conductivity between the two cells as the sample passes through one of the cells. The two cells are subjected to the same conditions, except for the presence of sample in the one cell, whereby the difference in electrical conductivity between the cells is directly attributed to the subject sample.

The Carlson U.S. Pat. No. 4,209,299 discloses the use of a single cell apparatus. When a single cell conductivity detector is used, a much greater reliance is placed on the stability of the baseline. Any changes in the conditions, such as temperature fluctuations or foreign substances, creates noises or drifts in the baseline. Additionally, when a single cell conductivity detector is used, such as disclosed by Carlson, high quality water is required since the presence of extraneous electrolytes interferes with signals from the conductive substance sought to be determined. An additional sample purification step is often required. When the detection of very low concentrations of a conductive volatile substance is desired, the purity requirement is heightened and the purification step becomes quite burdensome.

Additionally, conventional systems generally cannot tolerate samples with even moderate amounts of another dissolved substance such as salt, acid or sugar therein. These extraneous substances not only create noises in the baseline but also overwhelm the signal from the sample electrolytes.

Accordingly, a need exists for improved methods and apparatus for quantitative analysis of samples using electrical conductivity measuring techniques.

SUMMARY OF THE INVENTION

It is therefore an object of the present invention to provide methods and apparatus for quantitatively analyzing a sample using electrical conductivity measuring techniques, which methods and apparatus overcome disadvantages of the prior art. More particularly, it is an object of the present invention to provide methods and apparatus for quantitatively analyzing a sample using electrical conductivity measuring techniques wherein larger signals can be produced over a larger linear dynamic range as compared with conventional techniques, whereby detection of volatile substances at lower concentrations may be achieved. It is a further object of the invention to provide such methods and apparatus wherein even samples containing low quality water may be subjected to analysis without cumbersome water purification steps.

These and additional objects and advantages are provided by the methods and apparatus of the present invention.

Broadly, according to the methods of the present invention, the amount of volatile electrolyte present in an aqueous liquid sample is determined by transferring the electrolyte from the aqueous liquid sample to an absorber solution across a gas-permeable membrane which is non-passable to the aqueous liquid sample, and measuring the change in electrical conductivity of the absorber solution during the transfer period. The absorber solution contains a solute solvent which enhances the transfer of the electrolyte. The methods according to the present invention may be employed to determine the amount of a nonvolatile substance present in an aqueous sample by first converting the nonvolatile substance in the sample to a volatile substance. The methods of the present invention may also be employed for determining the amount of a volatile electrolyte present in a gaseous sample. The gaseous sample is passed through an air segmentation device wherein the volatile electrolyte is separated from the remaining gaseous sample, followed by either directly transferring the separated volatile electrolyte to an absorber solution across the gas-permeable membrane, or first dissolving the volatile electrolyte in deionized water to form an aqueous solution and then transferring the volatile electrolyte from the aqueous solution to an absorber solution across a gas-permeable membrane. The present invention is also directed to apparatus for achieving these methods.

The methods and apparatus of the invention are advantageous in several respects. The solute used on the absorber side of the membrane significantly facilitates the transport of volatile electrolytes across the membrane and improves the detection of transferred electrolytes. Additionally, the solute reduces the interference in the absorber solution and possibly generates a conductivity-enhancing complex with the compound. Furthermore, the solute on the absorber side may improve the signal detection limit, the linearity of the baseline and/or the reproducibility and autozeroing of the electrical conductivity cells.

In further embodiments, the methods and apparatus may employ a flow-through system, whereas a separate sample preparation step is not required. The sample may pass through an in-line sample preparation device, such as a gas segmentation device or a reduction cartridge, whereby the volatile substance may be separated from other gaseous components or produced by reaction of a nonvolatile substance with a reagent. Finally, the methods and apparatus of the invention may employ an electrical conductivity detector with a single cell design, without requiring extremely strict temperature control.

These and additional objects and advantages will be more fully apparent in view of the detailed description.

BRIEF DESCRIPTION OF THE DRAWINGS

The detailed description will be more fully understood in view of the drawings in which.

DETAILED DESCRIPTION

Figure 1:
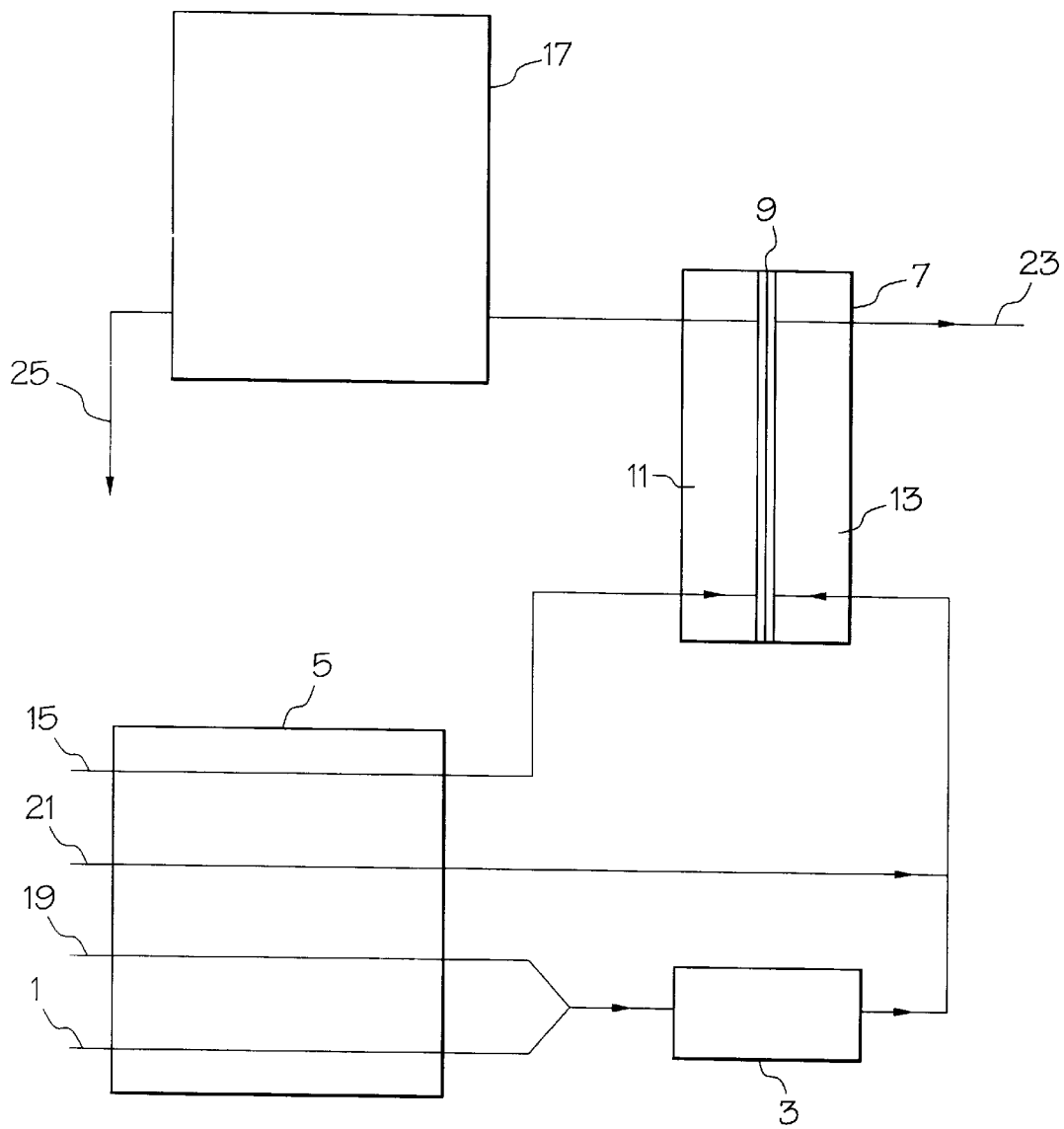
FIG. 1 is a schematic diagram of an apparatus according to the invention.
Figure 2:
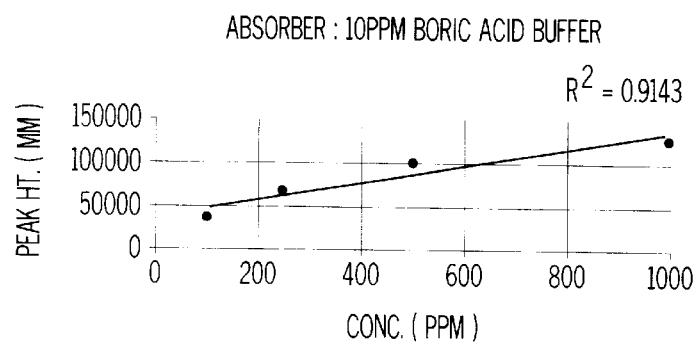
FIG. 2 is a graph of measurements made according to a method of the invention wherein the responses of the electrical conductivity detector, shown as peak heights of a strip chart recorder trace, are plotted against the concentrations of ammonia ion, in parts per million.
Figure 3:
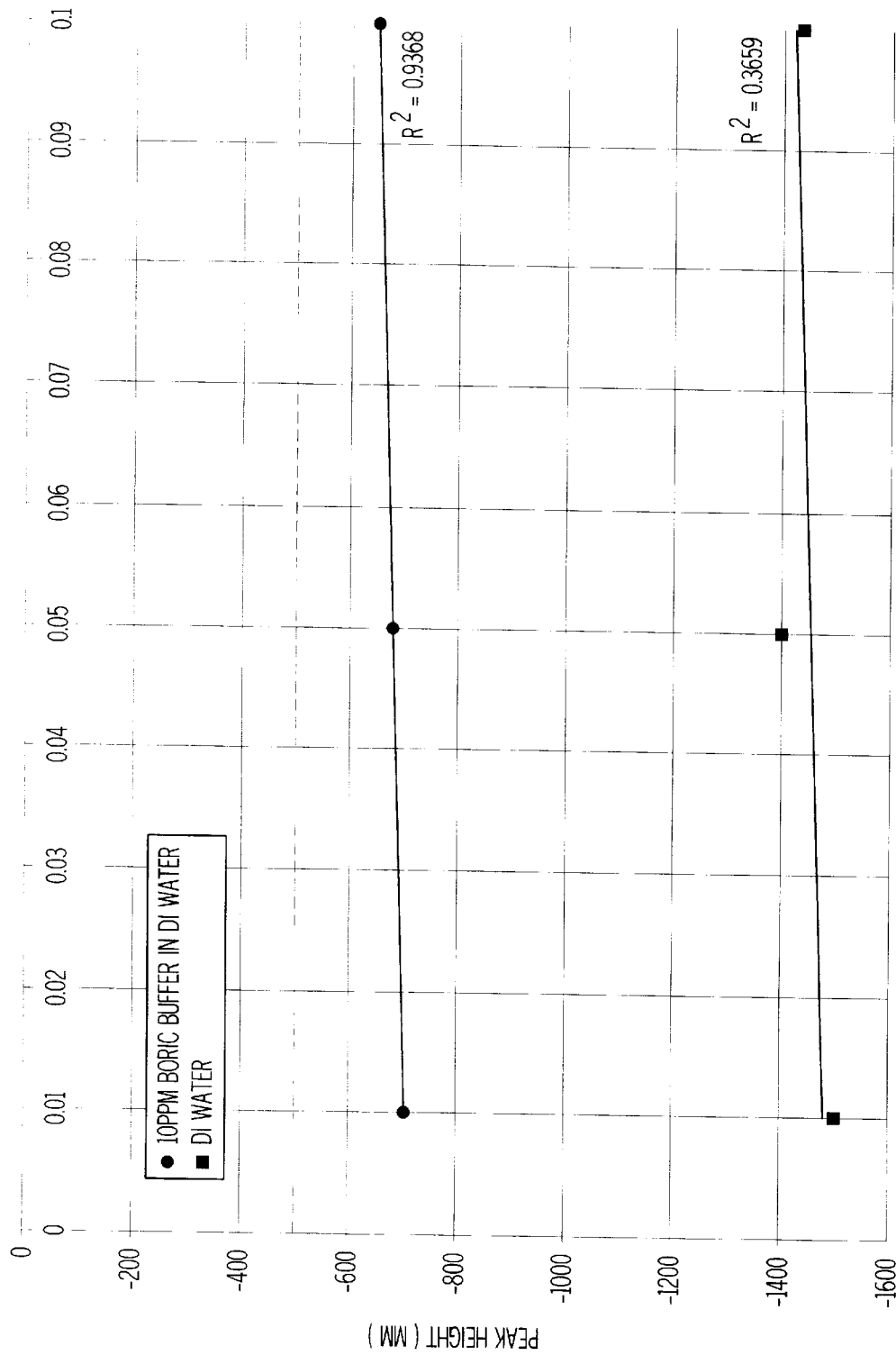
FIG. 3 is a graph of measurements made according to a method of the invention, particularly the responses of the electrical conductivity detector at low concentrations of ammonium ion using deionized water and buffer solution, respectively, as the absorber solution.

The present invention is directed to methods and apparatus for the quantitative analysis of an electrically conducting volatile substance in a sample. More particularly, a volatile substance passes through a gas-permeable membrane to an absorber solution which contains solute to enhance the transfer. The amount of the volatile substance in the absorber solution is then determined by measuring the conductivity change, for example, with a single cell electrical conductivity detector. The solute facilitates the transport of the volatile substance across the membrane and enhances the sensitivity of the electrical conductivity measurements.

The present invention is suitable for analysis of any compound that can pass through the gas permeable membrane, dissolve in water or other solvent and cause a detectable change in electrical conductivity of the resultant solution. More specifically, the present invention may be used for quantitative determination of nitrogen-containing compounds such as ammonia, nitrates, nitrites and urea. These compounds exist in drinking water, waste water, food, blood, soil and environmental samples. The present invention can also be used for the quantitative determination of gases such as carbon dioxide, nitrogen oxide, nitrogen dioxide, or ammonia. The present invention also may be employed for analysis of air samples. In-line reduction cartridges or gas segmentation devices may be used to convert a nonvolatile substance to a volatile substance, for example by means of a reduction reaction, or to separate a mixture of volatile substances, whereby extra sample preparation steps can be avoided. The present invention can be used as a selective gas analyzer as well as a solid sample analyzer.

In its broadest sense, the present invention comprises a method for determining the amount of volatile electrolyte present in an aqueous liquid sample. The method broadly comprises transferring the electrolyte from the aqueous liquid sample to an absorber solution across a gas-permeable membrane which is non-passable to the aqueous liquid sample, and measuring the change in electrical conductivity of the absorber solution during the transfer period. The absorber solution contains a solute which enhances the transfer of the electrolyte, and preferably also improves electrical conductivity measurements of the absorber solution. Preferably, the solute is selected from buffers and complexing agents for the volatile electrolyte substance. Suitable solutes include boric acid buffer, potassium hydrogen phosphate and the like. Other suitable solutes will be apparent to one of ordinary skill in the art depending on the particular chemical composition of the volatile electrolyte.

The methods according to the present invention are also directed to determining the amount of a non-volatile substance present in an aqueous liquid sample wherein the non-volatile substance in the aqueous liquid sample is converted into a volatile substance. For example, the aqueous liquid sample containing a non-volatile substance may be passed through a sample preparation device to convert the substance into a volatile electrolyte. In a preferred embodiment according to the present methods, the non-volatile substance may comprise a nitrate or a nitrite which is contacted with copper-coated zinc to convert the nitrate and/or nitrite to an ammonium ion. In an alternate preferred embodiment, the non-volatile substance is urea and conversion to a volatile electrolyte is achieved by contacting the urea with urease enzyme to form ammonium ion.

In a further embodiment, the methods of the present invention may be used to determine the amount of a volatile electrolyte present in a gaseous sample. The gaseous sample is first passed through a segmentation device wherein the subject volatile electrolyte is separated from the remainder of the gaseous sample. The volatile electrolyte is then dissolved in deionized water to form an aqueous solution and transferred from the aqueous solution to an absorber solution across a gas-permeable membrane as described above. The absorber solution comprises a solute which enhances the transfer of the electrolyte. The change in the electrical conductivity of the absorber solution is measured during the transfer. Alternatively, rather than dissolving the volatile electrolyte separated from the gaseous sample in the deionized water, the volatile electrolyte may be transferred directly across the membrane to the absorber solution. The absorber solution contains the solute to enhance the change in electrical conductivity of the absorber solution and facilitate measurement thereof.

A schematic embodiment of an apparatus for use in the methods of the invention is shown in FIG. 1. As shown in FIG. 1, an aqueous liquid sample 1 containing a substance to be quantitatively analyzed is transported to a reduction cartridge 3 by a pump 5, for example, a peristaltic pump. The reduction cartridge 3 contains a substance which reacts with the nonvolatile substance in the aqueous liquid sample to provide a volatile substance. For example, the reduction cartridge may contain cooper-coated zinc which will reduce nitrates or nitrites to ammonia. In another embodiment, the nonvolatile substance in the aqueous liquid sample is urea and urease enzyme is used in the reduction cartridge. The volatile substance is transported by the aqueous liquid sample stream to a permeation assembly 7. The permeation assembly 7 consists of a first chamber 11, a second chamber 13 and a gas-permeable membrane 9, which separates the two chambers. The gas-permeable membrane allows gases to pass therethrough, but is non-passable to the liquids. A suitable membrane is one formed of Teflon, although other suitable materials include silicone membranes and any other gas-permeable membrane known in the art.

An absorber solution 15 flows through the first chamber 11. The aqueous liquid sample stream containing the volatile substance is supplied to the second chamber 13. The volatile substance passes through the gas-permeable membrane 9 and dissolves in the absorber solution in the first chamber 11. Subsequently, the absorber solution flows to an electrical conductivity detector 17, which preferably is of the single cell type. The change in electrical conductivity of the absorber solution is measured and is representative of the amount of volatile electrolyte therein. The absorber solution then exits the electrical conductivity detector 17 through a first waste outlet 25 while the sample stream exits the second chamber 13 through a second waste outlet 23.

In accordance with an important feature, the absorber solution contains a solute which enhances the transfer of the volatile substance across the gas permeable membrane. The solute in the absorber solution also improves the signal detection limit as well as the linearity of the response and the reproducibility of the measurements. Suitable solutes will be apparent depending on the particular substance to be quantitatively analyzed. Preferably, the solute is either a buffer or a complexing agent. A boric acid buffer is preferred and consists of boric acid and ammonium borate. Alternatively, the buffer can be a potassium hydrogen phosphate. It is believed that the solute, i.e., the buffer solution, improves the sensitivity of the electrical conductivity measurements by reducing pH changes in the absorber solution that facilitate the transport of ammonia gas across the membrane, although the inventors do not intend to be bound by this theory.

In another embodiment, a caustic solution 19 is mixed with the aqueous liquid sample, to enhance the volatility of the volatile substance, for example ammonia, and suppress other components of the liquid sample. Alternatively, a caustic solution may be supplied directly to the second chamber 13 of the permeation assembly for these same benefits. The caustic solution preferably contains an alkali metal hydroxide solution. In the preferred embodiment, a potassium hydroxide solution is used.

While the particular equipment suitable for use in the methods of the invention will be apparent to those of ordinary skill in the art, several particular devices are preferred. For example, the pump 5 preferably is an eight-roller peristaltic pump with minimal pulsation and a constant velocity synchronous motor drive. The peristaltic pump is advantageous in that it can drive multiple streams of liquids or gases through the system of the present invention at a constant rate. In one embodiment, the reduction cartridge 3 preferably comprises a plastic syringe containing granular zinc. The zinc granules are plated with copper by contact with copper(II) sulfate solution. The conductivity detector preferably has a single straight through conductivity cell. The cell may be temperature controlled to within 0.01° Celsius with a heat exchanger on the inlet line. The zero circuit has a large dynamic range and very stable zero offset. The zero circuit and the temperature control are important when the absorber solution contains a buffer because the buffer creates a high background conductivity. A preferred conductivity detector is the Timberline 550 Model supplied by Timberline Instruments, Inc. of Boulder, Colo. It is preferred to conduct the methods of the invention by maintaining the conductivity detector temperature at 35° Celsius.

The liquid streams, such as the aqueous liquid sample, the absorber solution, the caustic solution, are transported in conventional tubings with conventional connectors joining the various components and tubings together, as will be apparent to those skilled in the art.

In one embodiment, wherein a volatile electrolyte in a gaseous sample is to be analyzed, the gaseous sample passes through an air segmentation device 21 shown in FIG. 1 wherein the volatile electrolyte substance is separated from the other gaseous components of the sample. In one embodiment, the separated volatile substance is dissolved in an aqueous solution which is transported by the pump 5 to the permeation assembly 7. In another embodiment, the volatile substance does not dissolve in the aqueous solution, but flows directly to the second chamber 13 of the permeation assembly where it is transferred across the permeation membrane.

According to another embodiment of the present invention, the absorber solution and/or the caustic solution is recycled. For example, the absorber solution exiting the electrical conductivity detector is returned to the absorber solution stream at a point upstream of the permeation assembly. Because the concentration of the volatile electrolyte in the absorber solution is relatively low in comparison with the concentration of the solute in the absorber solution, this recycling has little effect on the baseline of the electrical conductivity measurement. Therefore, running blank absorber solution through the system between sample runs is generally unnecessary, although it can be done occasionally as part of a maintenance routine.

The caustic solution can also be recycled to reduce system waste. The caustic solution exiting the permeation assembly can be returned to the original caustic solution stream at or upstream of a point before the caustic solution is mixed with the sample solution stream. The recycled caustic solution tends to dilute the caustic solution in a cumulative manner. That is, with each cycle through the system, the caustic solution is mixed with the sample solution in an aqueous solvent; the accumulation of the aqueous solvent from every cycle dilutes the caustic solution. This problem is reduced by using a small diameter tubing for the sample line so that smaller amounts of aqueous solvent are introduced into the caustic solution in each cycle. Occasionally, the pH of the caustic solution may be adjusted, for example, by adding caustic such as potassium hydroxide and DTPA (diethylenetriaminepentaacetic acid).

The following examples are set forth to illustrate specific embodiments of the methods and apparatus of the invention. Throughout the examples, parts and percentages are by weight unless otherwise specified.

EXAMPLE 1

This example illustrates the advantages of using a buffered absorber solution over a deionized (DI) water absorber solution in the detection of ammonium ions.

An apparatus similar to that shown in FIG. 1 is employed. The absorber solution contains 10 ppm of boric acid buffer in deionized (DI) water and its pH is adjusted to 7.01 by the addition of an ammonium hydroxide solution. For comparison, deionized water is used as the absorber solution in a comparative method. The caustic solution is prepared from 25 grams of potassium hydroxide and 5 grams of diethylenetriaminepentaacetic acid (DTPA) in 1 liter of DI water. The ammonium ion sample is prepared by dissolving ammonium acetate in DI water. No reduction cartridge or air segmentation device is used in this embodiment.

A peristaltic pump is used to simultaneously transport several streams through the system. The absorber solution is pumped into the first chamber 11 of the permeation assembly 7. The sample solution is premixed with the caustic solution before it is pumped into the second chamber 13 of the permeation assembly 7. The ammonium ion diffuses through the gas-permeable membrane and is dissolved in the absorber solution in the first chamber. The ammonium ion containing absorber solution then flows to a conductivity detector, where the change in electrical conductivity is measured and the signal is recorded on a strip chart recorder.

The detection limit is 1 ppb for both the buffered and unbuffered absorber solutions. However, the buffered absorber solution produces a more linear response in the lower concentration range than the pure DI water absorber solution.

EXAMPLE 2

This example demonstrates further compares the detection of ammonia gas using a boric acid buffered absorber solution.

A system similar to that shown in FIG. 1 is employed. The buffered absorber solution contains 10 ppm boric acid buffer in DI water and its pH is adjusted to 7.01 by the addition of an ammonium hydroxide solution. The ammonia gas sample is taken from the head space above an ammonium hydroxide solution.

The absorber solution is pumped into the first chamber 11 of the permeation assembly 7. Air runs through the second chamber 13 of the permeation assembly until it is dry. Then the ammonia gas is pumped directly into the second chamber and diffuses through the gas-permeable membrane to the first chamber, where it is dissolved in the absorber solution. The absorber solution is transported from the first chamber to the conductivity detector, where the change in electrical conductivity is measured and the signal is recorded on a strip chart recorder.

EXAMPLE 3

This example illustrates an embodiment of the present invention wherein the detection of nitrogen dioxide is achieved using DI water as the absorber solution, The caustic solution is prepared from 25 grams of potassium hydroxide and 5 grams of DTPA in one liter of water. The reduction cartridge contains granular zinc and is pre-treated with 10 milliliters of 0.1% copper(II) sulfate solution by injecting the copper sulfate solution through the reduction cartridge with a syringe.

The absorber solution is pumped into the first chamber 11 of the permeation assembly 7. The nitrogen dioxide is premixed with the caustic solution 19 before it is pumped into the reduction cartridge 3 in which the nitrogen dioxide is reduce to ammonia. After the resulting mixture passes through the reduction cartridge, it is pumped into the second chamber 13 of the permeation assembly 7. The ammonia diffuses through the gas-permeable membrane 9 and is dissolved in the absorber solution 15. The absorber solution then flows through the conductivity detector 17, where the change in electrical conductivity in the absorber solution is measured and the signal is recorded on a strip chart recorder.

Alternatively, nitrogen dioxide is dissolved in an aqueous stream where it is converted into electrically conductive ions by interaction with the water. The aqueous stream is then supplied to the second chamber and the analysis method continues as described above.

EXAMPLE 4

This example illustrates the improved detection of the ammonium ions using a potassium hydrogen phosphate (KHP) buffered absorber solution in accordance with the present invention, particularly as compared with a conventional method employing only a pure water absorber solution.

The absorber solution contains 100 ppm KHP in HPLC grade water and its pH is adjusted to 7.01 by the addition of potassium hydroxide. The pure water absorber solution used in the conventional method is pure HPLC grade water. The caustic solution is prepared from 25 grams of potassium hydroxide and 5 grams of DTPA in 1 liter of DI water. The ammonium sample is prepared by dissolving ammonium acetate in DI water. No reduction cartridge or air segmentation device is used to produce this sample.

The absorber solution is pumped into the first chamber 11 of the permeation assembly 7. The sample solution is premixed with the caustic solution before it is pumped into the second chamber 13 of the permeation assembly 7. The ammonium sample diffuses through the membrane and is dissolved in the absorber solution. The absorber solution then flows to the conductivity detector, where the change in electrical conductivity in the absorber solution is measured and the signal is recorded on a strip chart recorder.

When the buffered absorber solution is used, the detection limit for the ammonium ions is 1 ppm. In contrast, when HPLC water only is used as the absorber solution, a negative peak is observed at the same concentration of ammonium ions. The buffered absorber solution also has improved linearity of the signals when the concentrations of the ammonium ions are between 1 ppm and 20 ppm and when the concentrations of the ammonium ions are between 10 ppm and 100 ppm. In contrast, the HPLC water-only absorber solution does not show acceptable linear response until a much higher concentration range, for example between 100 ppm to 1000 ppm, is measured.

The responses from the buffered absorber solution are also greatly increased, even though the presence of buffer ions has created high background conductivity. Temperature control and stable zero baseline provide further improvement.

EXAMPLE 5

This example illustrates the improved detection of nitrate ions using a 10 ppm boric acid buffered absorber solution according to the present invention as compared to the conventional DI water-only absorber solution.

The buffered solution contains 10 ppm boric acid in DI water, and the pH is adjusted to 7.01 by the addition of ammonium hydroxide. The caustic solution is prepared from 25 grams of potassium hydroxide and 5 grams of DTPA in 1 liter of DI water. The nitrate sample is prepared by dissolving sodium nitrate in DI water and passing the sample solution through a reduction cartridge. The reduction cartridge contains granular zinc which has been treated with 10 milliliters of 0.1% copper(II) sulfate solution in a manner as described in Example 3.

The absorber solution is pumped into the first chamber 11 of the permeation assembly 7. The nitrate sample solution is mixed with the caustic solution before it is pumped into the reduction cartridge. From the reduction cartridge, the sample and caustic solution mixture is transported into the second chamber 13 of the permeation assembly 7. The nitrate ion diff-uses through the membrane and is dissolved in the absorber solution. The absorber solution then flows to a conductivity detector, where the change in electrical conductivity in the absorber solution is measured and the signal is recorded on a strip chart recorder.

When the buffered absorber solution is used, a nitrate concentration as low as 1 ppb is detectable. In contrast, the detection limit for the DI water-only absorber solution is 1 ppm. Another advantage of the buffered absorber solution is that a much improved linearity of the responses over the range of 100 ppb to 10 ppm of nitrate concentrations is achieved.

EXAMPLE 6

This example illustrates the long term stability of the baseline when the absorber solution and the caustic solution in the methods of the present invention are recycled. The recycling reduces waste generation and results in cost savings of reagents.

The buffered absorber solution contains 10 ppm boric acid in HPLC grade water and its pH is adjusted to 7.04 by the addition of potassium hydroxide. A comparative pure HPLC grade water absorber solution is employed in a comparative system. The caustic solution is prepared from 25 grams of potassium hydroxide and 5 grams of DTPA in 1 liter of DI water. The ammonium sample is prepared by dissolving ammonium acetate in DI water.

The absorber solution is pumped into the first chamber 11 of the permeation assembly 7. The sample solution is premixed with the caustic solution before it is pumped into the second chamber 13 of the permeation assembly 7. The ammonium ion diffuses through the membrane and is dissolved in the absorber solution. The absorber solution then flows to a conductivity detector where the change in electrical conductivity in the absorber solution is measured and the signal is recorded on a strip chart recorder.

After exiting the conductivity cell, the absorber solution is returned to the original absorber solution stream at a point upstream of the permeation assembly. The caustic solution is also recycled by returning the caustic solution that flows out of the permeation assembly to the original caustic solution stream at a point upstream of the permeation assembly.

When the pure water absorber solution is used, negative peaks are observed where the ammonium ion concentration is lower than 1 ppm. Though the buffer produces high background electrical conductivity, it also produces a flatter and less noisy baseline. The long term stability of the baseline also improves, even in the presence of sample in the recycled absorber solution, likely owing to the reduced accumulation of sample in the system by the buffer and/or owing to the relatively dilute concentration of sample ions in comparison with the buffer in the absorber solution. The long term stability of the baseline is advantageous in that it is not necessary to run blanks between samples. Thus, by the present invention, a large number of samples can be analyzed before it becomes necessary to readjust the zero baseline.

EXAMPLE 7

This example illustrates an embodiment directed towards the detection of ammonia in air. A liquid membrane cell is modified to accommodate a high gas flow rate on the sample side of the permeation assembly. The higher gas flow rate provides better response time and better detection limits. For a given concentration of ammonia in air, a higher flow rate of air will increase the amount of ammonia absorbed by the absorber solution that reaches the conductivity detector, thereby improving the detection limits.

Figure 4:
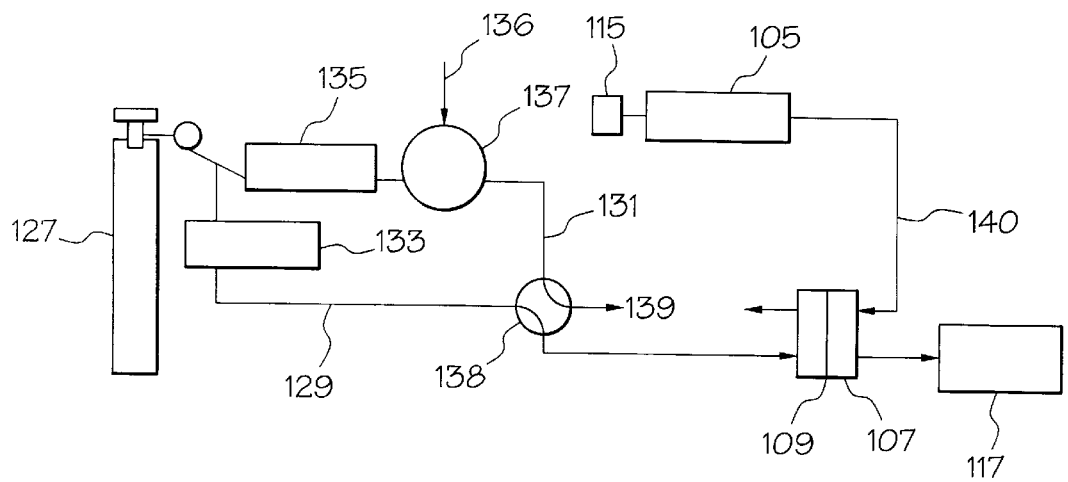
FIG. 4 is a schematic diagram of an embodiment for measuring an electrolyte in a gaseous sample.

The membrane cell 107 is set up in an ammonia detection system as shown in FIG. 4. The depth on the sample side of the membrane cell 107 is increased from 0.5 mm to 2.5 mm for the high gas flow rate. The absorber solution 115 contains 2 ppm boric acid in DI water, and the pH is adjusted to 7 by adding an ammonium hydroxide solution. The carrier gas, $N_2$, is supplied by a tank 127. The system was set up so there are two channels. The first channel 129 carries $N_2$ only and is provided with a flow meter 133, while the second channel 131 carries $N_2$ and ammonia and is provided with a flow meter 135, an ammonia supply line 136, and a permeation device 137. The ammonia is released from the permeation device 137 at a rate of 54 ng/min +/−25% at 30° C. The two channels meet at a valve 138 which directs one channel into the membrane cell and the other channel to the air via vent 139. The valve can be switched to direct either $N_2$, the baseline, or $N_2$ and $NH_3$, the sample to the membrane cell 107.

The Timberline 373 Diffusion Module Pump 105 is used to transport the absorber solution 115 into the membrane cell 107; the solution travels through a serpentine and out to the detector 117. The tubing 140 has an ID of 0.61 mm so the flow rate is about 1 ml/min. The sample enters, at a rate of 3 L/min of $N_2$, on the side of the cell membrane 109 opposite of the absorber solution. In between the two sides of the membrane cell 107, there is a gas permeable membrane 109, across which the ammonia diffuses. The ammonia dissolves into the absorber solution, and flows to the conductivity detector 117 where the change in electrical conductivity is measured.

The detection limit with this system is around 1 ppb ammonia in $N_2$. With the $N_2$ flow rate at 6 L/min and the permeation tube at 8° C. the concentration of ammonia is about 2.4 ppb, as calculated below:

Calculation of Concentration: permeation tube data: 20° C.=26 ng/min $Log\ P_1 = Log\ P_0 + \alpha(T_1 - T_0)$ $$P_0 = 26\ \ T_0 = 20\ \ T_1 = 8\ \ \alpha = .032\ \ P_1 = 11\,\text{ng/min}$$

$$\frac{11 \times 10^9\,\text{g/min}}{17} \times 22{,}400 = 1.05 \times 10^{-5}\,\text{cc/min of NH}_3$$

$$\frac{1.45 \times 10^{-5}\,\text{cc/min}}{6000\,\text{ml/min}} \times 100 = 2.4 \times 10^{-7}\,\%\,\text{NH}_3 = 2.4\,\text{ppb of NH}_3$$

Figure 5:
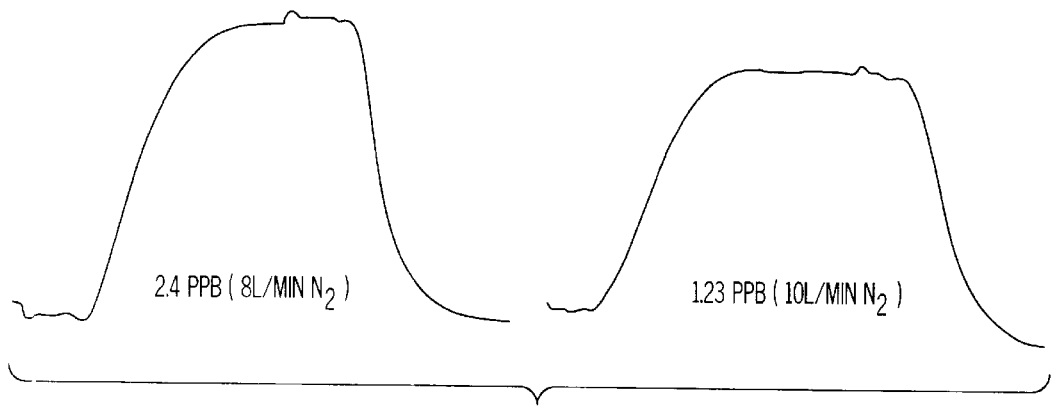
FIG. 5 is a diagram of detector tracings indicating transfer of electrolyte across a membrane.

A peak is detectable. By continuing to increase the flow of $N_2$ through the cell the concentration of ammonia becomes more dilute. The flow of $N_2$ is increased to 10 L/min with the temperature of the ice bath at 8° C. By doing this, the concentration of ammonia is decreased to 1.23 ppb. The peaks, as shown in FIG. 5, are nearly the same size, indicating there is almost complete transfer of ammonia across the membrane.

EXAMPLE 8

A tubular membrane may be used for the analysis of electrolytes in gaseous or liquid samples. The membrane assembly can be constructed of low cost disposable plastic tubing, plastic tees, and connectors. This simplifies the installation of the membrane cell and increases membrane life. The porous polytetrafluoroethylene (PTFE) tubing is much more rugged than the flat membrane material.

Figure 6:
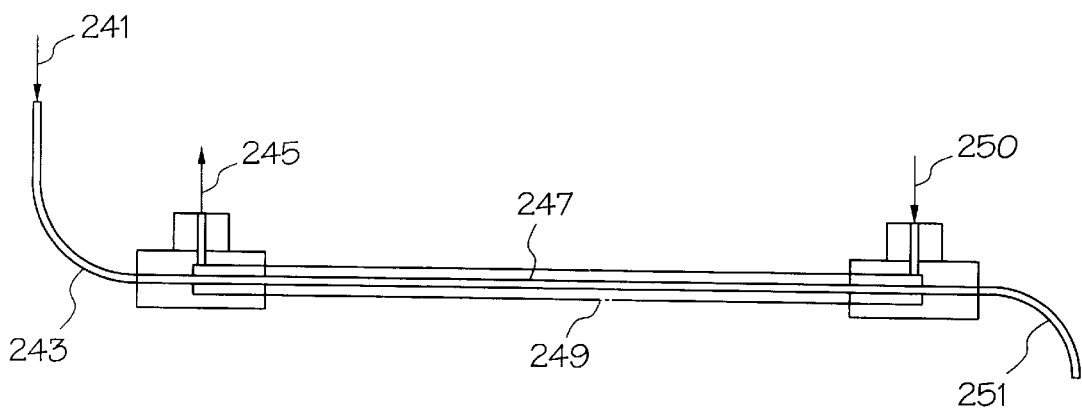
FIG. 6 is a schematic diagram of an embodiment for measuring an electrolyte in a sample using a tubular membrane.

As shown in FIG. 6, a porous PTFE tubular membrane 247 is located within solid tubing 249, preferably the solid tubing is Teflon. A gas, such as air or nitrogen, carrying the compound to be measured, such as ammonia, flows in the direction of arrow 250 through the space between the solid tubing 249 and the porous PTFE tubular membrane 247, and exits through vent 245. Absorber solution from the pump flows in the direction of arrow 241 through solid tubing 243, preferably solid Teflon tubing, into the tubular membrane 247, flows through the tubular membrane 247, and exits through solid tubing 251, preferably solid Teflon tubing, to the detector.

This example illustrates the advantages of a tubular membrane for analysis of ammonia in air or liquid samples. Preferably the porous PTFE membrane 247 has an ID =1.1 mm and an OD=1.8 mm. The tubular membrane 247 has the absorber solution flowing through it at 1 ml/min; the absorber solution flows through the tubular membrane 247 and then into the detector. The tubular membrane 247 is placed inside a Teflon tube 249 that has a mixture of $N_2$ and $NH_3$ flowing through it at 3 L/min. The ammonia is absorbed through the membrane 247 into the absorber solution from the surrounding $N_2$ gas.

Figure 7:
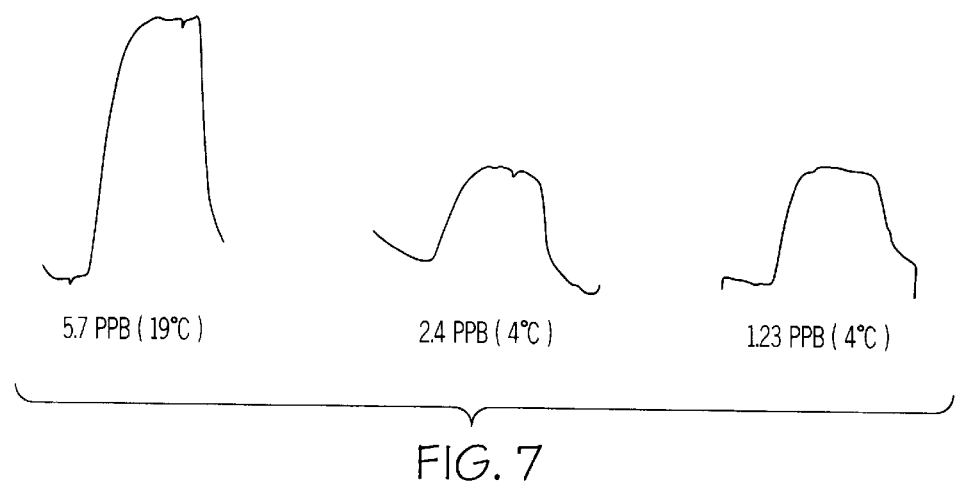
FIG. 7 is a diagram of detector tracings indicating transfer of electrolyte across a tubular membrane.

The system is tested at 19° C. with 6 L/min of gas flow, at 4° C. with 6 L/min of gas flow, and at 4° C. with 10 L/min of gas flow. These concentrations, 5.7 ppb, 2.4 ppb, 1.23 ppb respectively, are easily detectable and the response time is much shorter than with any other tested PTFE tubular membranes. Strip chart results are shown in FIG. 7.

The examples and the specific embodiments of the invention described herein are presented to further illustrate the invention and are not intended to be limiting thereof. Additional embodiments and advantages of the present invention will be apparent to those skilled in the art and are within the scope of the claimed invention.

What is claimed is:

1. A method for determining the amount of volatile electrolyte present in an aqueous liquid sample, comprising:
    providing the aqueous sample in a flowing stream in a continuous flow system;
    transferring the electrolyte from the aqueous liquid sample in the flowing stream to a flowing stream of an absorber solution across a gas-permeable membrane which is non-passable to the aqueous liquid sample; and
    measuring the change in electrical conductivity of the absorber solution during the transfer period, wherein said absorber solution contains a solute which enhances the transfer of the electrolyte.

2. The method as in claim 1, wherein the solute is selected from the group consisting of a buffer and a complexing agent.

3. The method as in claim 2, wherein the buffer is a boric acid buffer.

4. The method as in claim 2, wherein the buffer is potassium hydrogen phosphate.

5. A method for determining the amount of a nonvolatile nitrogen-containing substance present in an aqueous liquid sample, the method comprising:
    providing the aqueous sample in a flowing stream in a continuous flow system;
    converting the nonvolatile nitrogen-containing substance in the aqueous liquid sample into a volatile substance comprising ammonia ion;
    transferring the volatile substance from the aqueous liquid sample in the flowing stream to a flowing stream of an absorber solution across a gas-permeable membrane which is non-passable to the aqueous liquid sample, wherein the absorber solution comprises a solute which enhances the transfer of the electrolyte; and
    measuring the change in electrical conductivity of the absorber solution.

6. The method as in claim 5, wherein the solute is selected from the group consisting of a buffer and a complexing agent.

7. The method as in claim 6, wherein the buffer is a boric acid buffer.

8. The method as in claim 6, wherein the buffer is potassium hydrogen phosphate.

9. The method as in claim 5, wherein the non-volatile substance is selected from the group consisting of nitrates and nitrites, and the converting step comprises passing the nonvolatile substance through a sample preparation device comprising copper-coated zinc.

10. The method as in claim 5, wherein the non-volatile substance is urea, and the converting step comprises passing the nonvolatile substance through a sample preparation device comprising urease enzyme.

11. The method as in claim 5, wherein the converting step comprises passing the nonvolatile substance through a sample preparation device comprising a caustic solution.

12. The method as in claim 11, wherein the caustic solution comprises an alkali metal hydroxide solution.

13. A method for determining the amount of a volatile electrolyte present in a gaseous sample, the method comprising:
    passing the gaseous sample through a segmentation device wherein the volatile electrolyte is separated from the gaseous sample;
    dissolving the volatile electrolyte in deionized water to form an aqueous solution;
    providing the aqueous solution in a flowing stream in a continuous flow system;
    transferring the volatile electrolyte from the aqueous solution in the flowing stream to a flowing stream of an absorber solution across a gas-permeable membrane which is non-passable to the aqueous solution, wherein the absorber solution comprises a solute which enhances the transfer of the electrolyte; and
    measuring the change in electrical conductivity of the absorber solution.

14. The method as in claim 13, wherein the solute is selected from the group consisting of a buffer and a complexing agent.

15. The method as in claim 14, wherein the buffer is a boric acid buffer.

16. The method as in claim 14, wherein the buffer is potassium hydrogen phosphate.

17. A method for determining the amount of a volatile electrolyte present in a gaseous sample, the method comprising:
    passing the gaseous sample through a segmentation device whereby the volatile electrolyte is separated from the gaseous sample;
    transferring the volatile electrolyte across a gas-permeable membrane to a flowing stream of an absorber solution, wherein the membrane is non-passable to the absorber solution;
    dissolving the volatile electrolyte in the flowing stream of the absorber solution, wherein the absorber solution comprises a solute which enhances the transfer of the electrolyte; and
    measuring the change in electrical conductivity of the absorber solution.

18. The method as in claim 17, wherein the solute is selected from the group consisting of a buffer and a complexing agent.

19. The method as in claim 18, wherein the buffer is a boric acid buffer.

20. The method as in claim 18, wherein the buffer is potassium hydrogen phosphate.

21. A continuous flow apparatus for determining the amount of a volatile electrolyte in an aqueous liquid sample stream, the apparatus comprising:
    a flowing stream of an aqueous liquid sample comprising a volatile electrolyte;
    a flowing stream of caustic solution;
    a flowing stream of absorber solution;
    a pump for simultaneously feeding the three streams at a constant flow rate;
    a permeation assembly connected downstream from the pump and divided into first and second chambers by a gas-permeable membrane, the gas-permeable membrane allowing a gas to pass therethrough and preventing an aqueous liquid from passing therethrough;
    means for directing the absorber solution stream through the first chamber and the aqueous liquid stream and the caustic solution stream through the second chamber; and an electrical conductivity detector for determining the electrical conductivity of the absorber solution after transfer of the volatile electrolyte from the aqueous liquid sample stream to the absorber solution stream, wherein the absorber solution stream contains a solute which enhances the transfer of the electrolyte.

22. An apparatus as in claim 21, further comprising:

first recycling means downstream of the electrical conductivity detector for recycling absorber solution; and second recycling means downstream of the permeation assembly for recycling the caustic solution.

23. An apparatus as in claim 21, further comprising:

a reduction cartridge arranged between the pump and the permeation assembly for converting a nonvolatile component of the aqueous liquid sample into the volatile electrolyte.

24. An apparatus as in claim 21, further comprising a segmentation device for supplying a volatile component to the aqueous liquid sample stream.

25. A method for determining the amount of volatile electrolyte comprising ammonia ion present in an aqueous liquid sample, comprising:

providing the aqueous sample in a flowing stream in a continuous flow system;

transferring the electrolyte from the aqueous liquid sample in the flowing stream to a flowing stream of an absorber solution across a gas-permeable membrane which is non-passable to the aqueous liquid sample; and measuring the change in electrical conductivity of the absorber solution during the transfer period, wherein said absorber solution contains boric acid buffer.

26. A method for determining the amount of a nonvolatile nitrogen-containing substance present in an aqueous liquid sample, the method comprising:

providing the aqueous sample in a flowing stream in a continuous flow system;

converting a nonvolatile nitrogen-containing substance in the aqueous liquid sample into a volatile substance comprising an ammonia ion;

transferring the volatile substance from the aqueous liquid sample in the flowing stream to a flowing stream of an absorber solution across a gas-permeable membrane which is non-passable to the aqueous liquid sample, wherein the absorber solution comprises boric acid buffer; and measuring the change in electrical conductivity of the absorber solution.

27. A method for determining the amount of a volatile electrolyte comprising ammonia ion present in a gaseous sample, the method comprising:

passing the gaseous sample through a segmentation device wherein the volatile electrolyte is separated from the gaseous sample;

dissolving the volatile electrolyte in deionized water to form an aqueous solution;

providing the aqueous solution in a flowing stream in a continuous flow system;

transferring the volatile electrolyte from the aqueous solution in the flowing stream to a flowing stream of an absorber solution across a gas-permeable membrane which is non-passable to the aqueous solution, wherein the absorber solution comprises boric acid buffer; and measuring the change in electrical conductivity of the absorber solution.

28. A method for determining the amount of a volatile electrolyte comprising ammonia ion present in a gaseous sample, the method comprising:

passing the gaseous sample through a segmentation device whereby the volatile electrolyte is separated from the gaseous sample;

transferring the volatile electrolyte across a gas-permeable membrane to a flowing stream of an absorber solution, wherein the membrane is non-passable to the absorber solution;

dissolving the volatile electrolyte in the flowing stream of the absorber solution, wherein the absorber solution comprises boric acid buffer; and measuring the change in electrical conductivity of the absorber solution.

* * * * *